United States Patent
Mei

(10) Patent No.: US 11,484,207 B2
(45) Date of Patent: Nov. 1, 2022

(54) METHOD AND SYSTEM FOR CORRECTING FOCUS LOCATION IN MAGNETIC RESONANCE GUIDED FOCUSED ULTRASOUND SURGERY

(71) Applicant: Soochow University (Taiwan R.O.C.), Taipei (TW)

(72) Inventor: Chang-Sheng Mei, Taipei (TW)

(73) Assignee: Soochow University, Taipei City (TW)

(*) Notice: Subject to any disclaimer, the term of this patent is extended or adjusted under 35 U.S.C. 154(b) by 894 days.

(21) Appl. No.: 16/361,323

(22) Filed: Mar. 22, 2019

(65) Prior Publication Data
US 2019/0320904 A1    Oct. 24, 2019

Related U.S. Application Data

(60) Provisional application No. 62/654,290, filed on Apr. 6, 2018.

(51) Int. Cl.
*A61B 5/00* (2006.01)
*A61B 5/055* (2006.01)
(Continued)

(52) U.S. Cl.
CPC ............ *A61B 5/0036* (2018.08); *A61B 5/055* (2013.01); *A61B 17/320068* (2013.01);
(Continued)

(58) Field of Classification Search
CPC .................. A61B 5/0036; A61B 5/055; A61B 17/320068; A61B 5/015;
(Continued)

(56) References Cited

U.S. PATENT DOCUMENTS

| 6,377,834 B1* | 4/2002 | Zhou | A61B 5/055 324/315 |
| 6,445,183 B1* | 9/2002 | Shimizu | A61B 5/055 324/309 |

(Continued)

FOREIGN PATENT DOCUMENTS

| CN | 100335005 C | 9/2007 |
| CN | 102077108 A | 5/2011 |

OTHER PUBLICATIONS

Mei et al., "Accurate Field Mapping in the Presence of B0 Inhomogeneities. Applied to MR Thermometry" Magnetic Resonance in Medicine 73:2142-2151 (2015).

*Primary Examiner* — Baisakhi Roy
(74) *Attorney, Agent, or Firm* — Hsuanyeh Law Group P.C.

(57) ABSTRACT

The present disclosure provides a method for determining an ultrasound focus location in a thermal image. In one aspect, the method includes obtaining a magnetic resonance thermal image of a tissue heated by a focused ultrasound and correcting a chemical shift and a k-space shift of a monitored ultrasound focus location in the magnetic resonance thermal image such that the monitored ultrasound focus location is aligned with a real physical ultrasound focus location. Correcting the chemical shift includes correcting a first spatial error of the monitored ultrasound focus location caused by resonance frequency changes of hydrogen nuclei due to environmental differences of water molecules. Correcting the k-space shift includes correcting a second spatial error of the monitored ultrasound focus location caused by temperature error due to spatial variations of a primary magnetic field.

6 Claims, 9 Drawing Sheets

(51) Int. Cl.
*A61B 17/32* (2006.01)
*G01R 33/565* (2006.01)
*G01R 33/56* (2006.01)
*G01R 33/48* (2006.01)
*A61N 7/02* (2006.01)
*A61B 17/00* (2006.01)

(52) U.S. Cl.
CPC ........... *A61N 7/02* (2013.01); *G01R 33/4804* (2013.01); *G01R 33/4814* (2013.01); *G01R 33/5608* (2013.01); *G01R 33/56527* (2013.01); *A61B 2017/00084* (2013.01); *A61B 2017/320069* (2017.08)

(58) Field of Classification Search
CPC ......... A61B 2017/00084; A61B 2017/320069; A61B 2018/00791; A61B 2090/374; A61N 7/02; G01R 33/4804; G01R 33/4814; G01R 33/5608; G01R 33/56527
See application file for complete search history.

(56) References Cited

U.S. PATENT DOCUMENTS

| | | | | |
|---|---|---|---|---|
| 8,229,544 | B2* | 7/2012 | Tseng | G01R 33/4804 324/315 |
| 8,498,461 | B2* | 7/2013 | Gross | G01R 33/4828 382/128 |
| 2005/0065429 | A1* | 3/2005 | Zhou | G01R 33/4804 600/412 |
| 2008/0292167 | A1* | 11/2008 | Todd | G01R 33/4804 382/131 |
| 2016/0157828 | A1* | 6/2016 | Sumi | G01N 29/46 702/189 |
| 2017/0035301 | A1* | 2/2017 | Lechner-Greite | G01R 33/4804 |
| 2017/0322274 | A1* | 11/2017 | Bolster, Jr | G01R 33/5615 |
| 2019/0129026 | A1* | 5/2019 | Sumi | G01S 7/52033 |
| 2019/0320904 | A1* | 10/2019 | Mei | A61B 17/320068 |

* cited by examiner

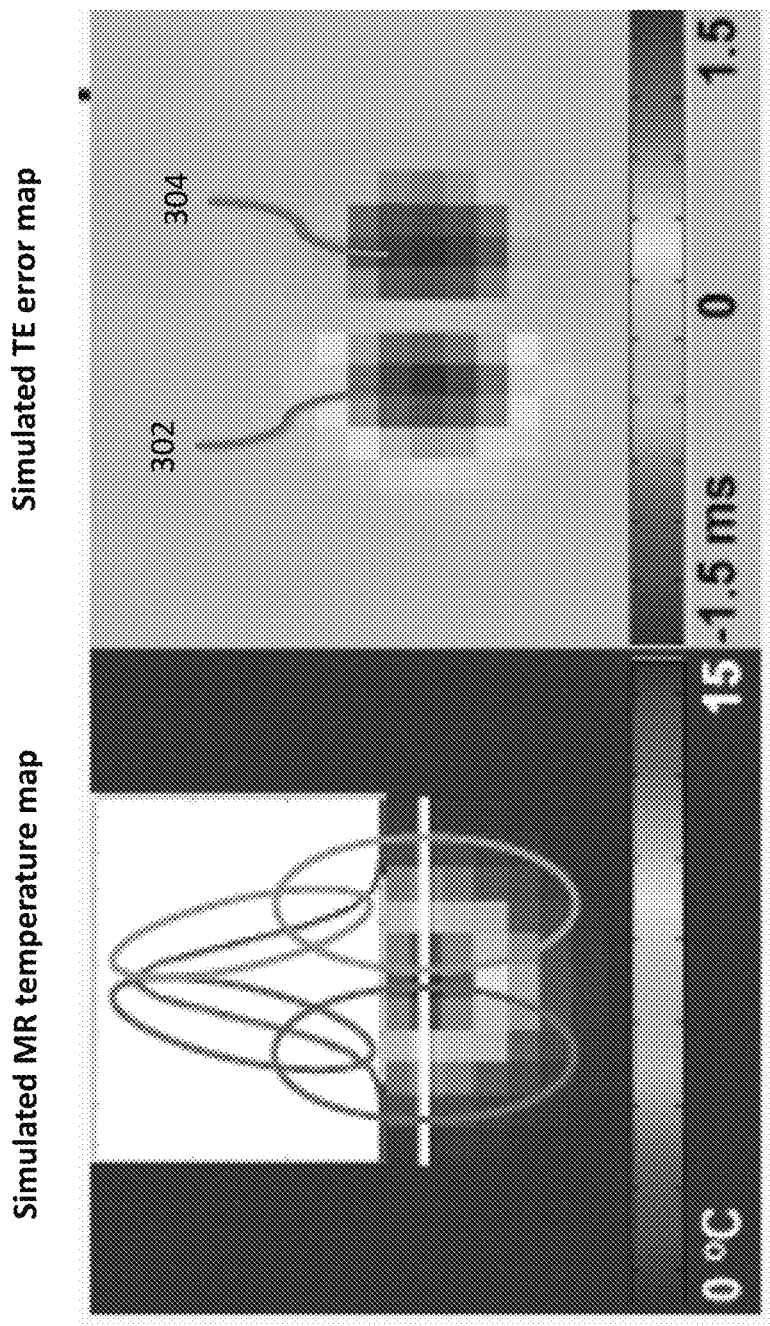

Original  After chemical shift correction  After k-space shift correction

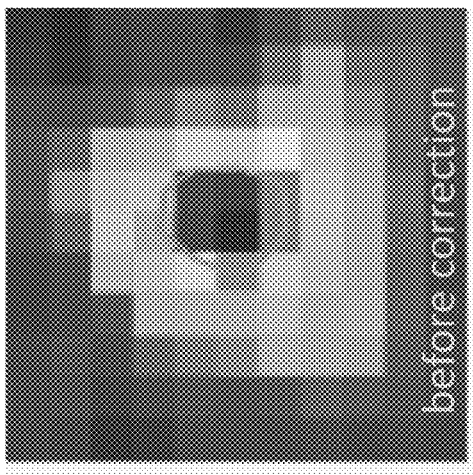
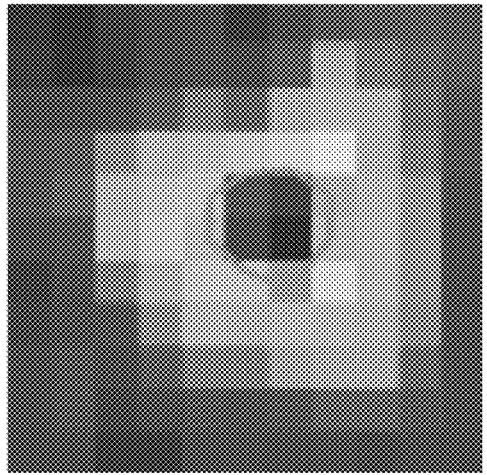
FIG. 9a
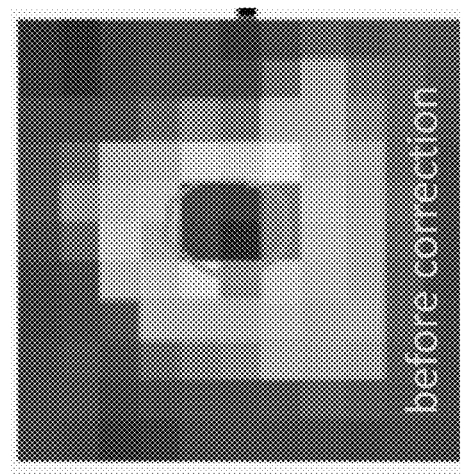
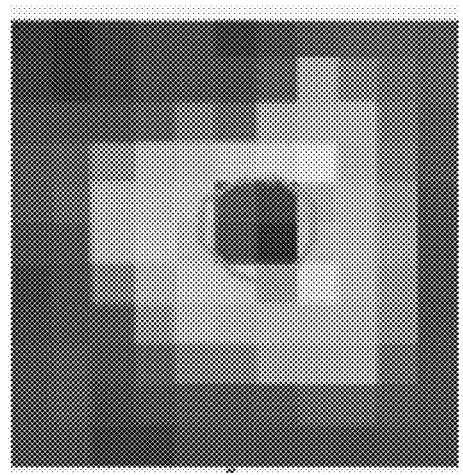
FIG. 9b

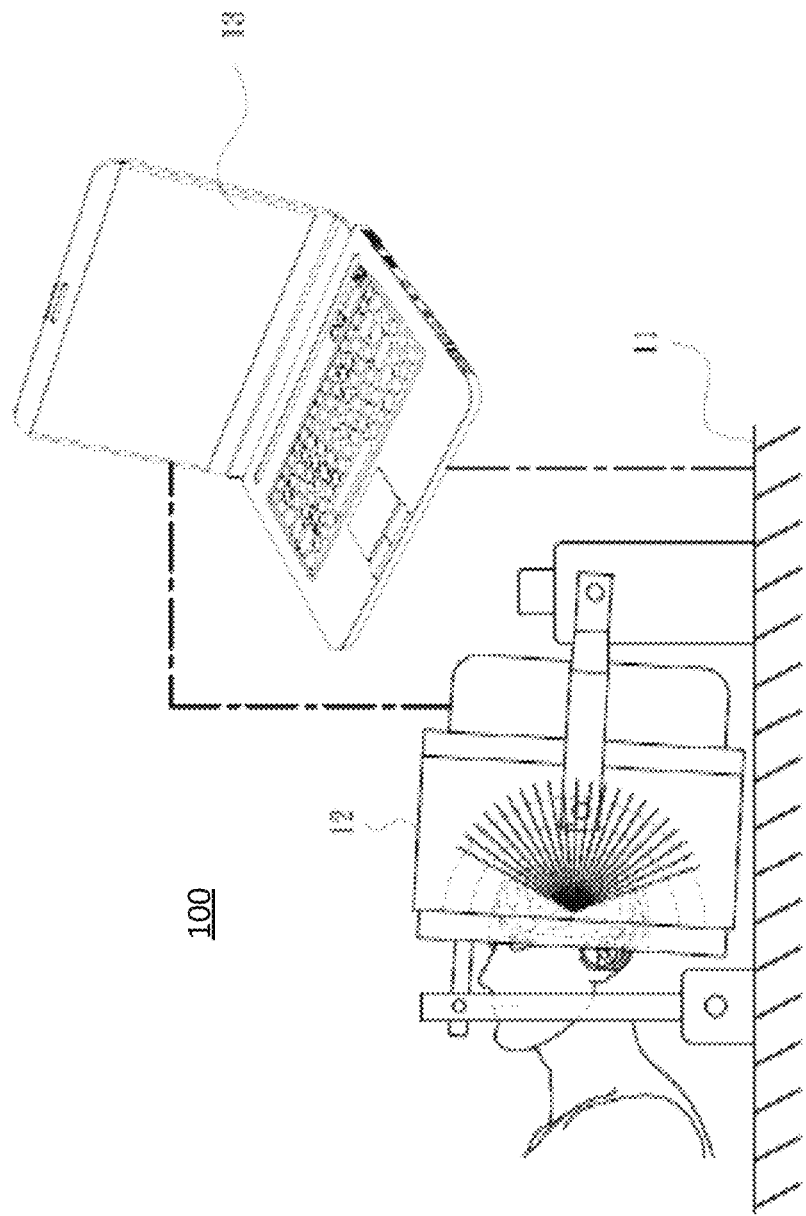

METHOD AND SYSTEM FOR CORRECTING FOCUS LOCATION IN MAGNETIC RESONANCE GUIDED FOCUSED ULTRASOUND SURGERY

RELATED APPLICATIONS

This application claims the benefit of priority to U.S. Provisional Application No. 62/654,290, filed on Apr. 6, 2018, the entire contents of which are incorporated herein by reference for all purposes.

TECHNICAL FIELD

The present disclosure relates to a method and a system for correcting focus location of focused ultrasound. More particularly, the present disclosure relates to a method and a system for correcting focus location of magnetic resonance guided focused ultrasound (MRgFUS).

BACKGROUND

High Intensity Focused Ultrasound (HIFU) is a non-invasive surgical treatment, which employs ultrasound energy to thermally ablate the target tissue selectively while being guided in real time by thermal images of Magnetic Resonance Imaging (MRI) so as to monitor and adjust the thermal dosage. To plan, monitor, and assess the performance of this treatment, this surgery must be done under magnetic resonance imaging (MRI), which is why this surgery is named magnetic resonance guided focused ultrasound (MRgFUS) surgery.

This surgical resection is effective to treat, e.g., essential tremor, uterine fibroids, etc. Using essential tremor as an example, after the thalamotomy is found using magnetic resonance imaging, focused ultrasound ablation is performed to a target tissue (ventral intermediate nucleus) within the thalamotomy while being monitored simultaneously using MRI thermal imaging. Because the target tissue is very small in size, it is quintessentially important to accurately aim at the target tissue. Because the surgery uses MR thermal imaging to locate the target tissue and monitor the thermal dosage, image artifacts in the MRI thermal images may cause the focus location to appear spatially displaced in the MR temperature maps, thereby resulting in spatial errors between the focus location on the MRI thermal image and the actual focus location.

One well-known reason is that "heating" itself causes magnetic property changes, which causes spatial deviation of hot spots in MRI thermal images. Another reason is that heating creates MRI phase gradient in real space, which causes k-space errors in MRI signals, which in turn causes temperature error (Mei, C. S., et al. "Accurate field mapping in the presence of B0 inhomogeneities, applied to MR thermometry," Magn. Reson. Med., 2015; 73(6):2142-51). We found that the polarity of temperature error at two sides of the focal point is completely inverse to each other, which results in the shifting of hot spots in MRI thermal images. For the two reasons stated above, the heating point appeared on the monitored thermal image would differ from the actual heating point, and the higher the heating temperature, the more the spatial displacement.

Currently, clinical solutions to these problems are dangerous and slow. As discussed above, image artifacts in MRI thermal images causes misalignment of focus locations on the thermal images, thereby resulting in errors of target location. Because errors only occur along the MRI's frequency-encoding direction, in practice, low acoustic power sonication is first applied to a patient's target tissue and monitored by two-dimension MRI thermal imaging to confirm the focus location along non-frequency-encoding direction, so as to complete accurate alignment of focus location in one dimension. To complete accurate alignment of focus location in another dimension, low acoustic power sonication is again applied to the same target tissue with the frequency-encoding direction being swapped with non-frequency-encoding direction in MRI thermal imaging.

In each alignment, the physician must observe the patient's response to decide whether the adjustment is appropriate; and in each adjustment, at least two low power sonication processes are required to confirm that the actual application location matches with the heating location in the MRI thermal image. Despite that low power sonication is used and that misalignment scale is small, such back and forth (trial and error) heating processes can still cause damages to the patient and prolong the overall treatment time. Moreover, even if the alignment is completed, the heating temperature change can still cause shifting of focal hot spot in the thermal image. That is, without proper corrections, the focus location in the thermal image is actually always wrong. This largely reduces the meaning of MRI guided surgery.

The so-called "chemical shift" is one of the reasons for the location misalignment between the focus location appeared in MRI thermal images and the actual focus/heating location in the thalamus target. Chemical shift originates from the differences in Larmor frequency of the heated tissue, thereby resulting in the location error in the MRI thermal image along the frequency encoding direction. This is the most well-known error so far, but the correction of chemical shift error alone cannot quantitatively explain the amount of error in clinical observation. Particularly, in applications that require high targeting accuracy, such as the treatment of Essential Tremor, ablation at an erroneous location would affect the treatment efficacy, even resulting in total failure of the surgery. Therefore, there is a need to provide a fast and straightforward error correction method in the medical field that requires ultra-high targeting accuracy, so as to enhance the alignment accuracy of high intensity focused ultrasound (HIFU) surgery.

SUMMARY

In view of the above, one objective of the present disclosure is to develop an MR strategy with high spatial precision of focus, making the alignment process more straightforward and intuitive. This technique is not just capable of quickly aligning the focus with the target at the surgery planning stage, but also, at the treating stage, it can automatically detect and correct any extra spatial offset, due to its temperature dependency, and then fine tune the alignment.

In one aspect, the present disclosure provides a method for determining an ultrasound focus location in a thermal image, the method comprising: obtaining a magnetic resonance thermal image of a tissue heated by a focused ultrasound; and correcting a chemical shift and a k-space shift of a monitored ultrasound focus location in the magnetic resonance thermal image such that the monitored ultrasound focus location is aligned with a real physical ultrasound focus location; wherein correcting the chemical shift comprises correcting a first spatial error of the monitored ultrasound focus location caused by resonance frequency changes of hydrogen nuclei due to environmental differences of water molecules; and wherein correcting the k-space shift comprises correcting a second spatial error of the monitored ultrasound focus location caused by temperature error due to spatial variations of a primary magnetic field.

In one embodiment, the magnetic resonance thermal image is a two-dimensional temperature map having M-by-N pixels, where M and N are natural numbers.

In one embodiment, correcting the second spatial error comprises correcting a temperature error for each of the M-by-N pixels of the two-dimensional temperature map based on a corrected echo time.

In one embodiment, the temperature error is derived from the following formula:

$$\Delta T(\vec{r}) = \Delta\theta(\vec{r})/(\gamma\alpha B_0 \cdot TE(\vec{r}))$$

where $\Delta T(\vec{r})$ is a temperature change between a measured time frame and a baseline at position $\vec{r}$, $\Delta\theta(\vec{r})$ is a phase difference between the measured time frame and the baseline, $\gamma$ is a gyromagnetic ratio, $\alpha$ is a heating-induced proton resonance frequency (PRF) change coefficient, $B_0$ is a main magnetic field strength, and $TE(\vec{r})$ is the corrected echo time of one of the M-by-N pixels at position $\vec{r}$.

In one embodiment, the corrected echo time at position $\vec{r}$ is derived from the following formula:

$$TE(\vec{r}) = TE + \Delta TE(\vec{r})$$

where TE is a nominal echo time initially defined by a user, and $\Delta TE(\vec{r})$ is an echo time error at position $\vec{r}$.

In one embodiment, the echo time error at position $\vec{r}$ is defined by the following formula:

$$\Delta TE(\vec{r}) = N_f \times \nabla_x(\Delta\theta(\vec{r}))/BW/2\pi$$

where $N_f$ is a matrix size of the magnetic resonance thermal image along a frequency encoding direction, $\nabla_x(\Delta\theta(\vec{r}))$ is a spatial gradient of a phase difference at position $\vec{r}$ along the frequency encoding direction, $\Delta\theta(\vec{r})$ is a phase difference upon subtraction of the magnetic resonance thermal image prior to heating, and BW is a total receiver bandwidth of the magnetic resonance thermal image.

In one embodiment, correcting the chemical shift and the k-space shift comprises correcting the chemical shift either before or after correcting the k-space shift.

In another aspect, the present disclosure provides an apparatus for thermally ablating a tissue, the apparatus comprising: a focused ultrasound device configured to generate focused ultrasound so as to heat a target tissue at an actual ultrasound focus location of the focused ultrasound; a magnetic resonance imaging device configured to generate a magnetic resonance imaging data of the target tissue; and a computer device configured to generate a magnetic resonance thermal image based on the magnetic resonance imaging data so as to display a monitored ultrasound focus location of the focused ultrasound on the magnetic resonance thermal image; wherein the computer device is further configured to correct a chemical shift and a k-space shift of the monitored ultrasound focus location in the magnetic resonance thermal image such that the monitored focus location is aligned with the actual ultrasound focus location; wherein the chemical shift is corrected by calculating a first spatial error of the monitored ultrasound focus location caused by resonance frequency changes of hydrogen nuclei due to environmental differences of water molecules; and wherein the k-space shift is corrected by calculating a second spatial error of the monitored ultrasound focus location caused by temperature error due to spatial variations of a primary magnetic field.

In still another aspect, the present disclosure provides a computer program product for determining an ultrasound focus location in a thermal image, the computer program product when executed by a computer device causing the computer device to perform a method comprising: obtaining a magnetic resonance thermal image of a tissue heated by a focused ultrasound; and correcting a chemical shift and a k-space shift of a monitored ultrasound focus location in the magnetic resonance thermal image such that the monitored ultrasound focus location is aligned with a real physical ultrasound focus location; wherein correcting the chemical shift comprises correcting a first spatial error of the monitored ultrasound focus location caused by resonance frequency changes of hydrogen nuclei due to environmental differences of water molecules; and wherein correcting the k-space shift comprises correcting a second spatial error of the monitored ultrasound focus location caused by temperature error due to spatial variations of a primary magnetic field.

BRIEF DESCRIPTION OF THE DRAWINGS

FIGS. 3a and 3b illustrate a focal point on an MRI temperature map and an echo time error map at two sides of the focal point.

FIGS. 9a and 9b illustrates a comparison of focus location in view of the correction orders of the chemical-shift correction and the k-space shift correction.

FIG. 10 illustrates a system diagram in accordance with an embodiment of the present disclosure.

DETAILED DESCRIPTION

Except otherwise defined herein, the technical and scientific terminologies used in this specification refer to the plain and ordinary meaning as understood by one of ordinary skill in the art.

The embodiments set forth herein are only to illustrate the technical ideas and features of the present disclosure, such that one of ordinary skill in the art can understand the content of this invention and to implement the invention accordingly, and not to limit the scope of this claimed invention. Any equivalent changes and/or modification in accordance with the spirit of this invention shall fall within the scope of this claimed invention.

In MRgFUS surgery, high intensity focused ultrasound (HIFUS) is used to heat and thermally ablate target tissue so as to treat diseases. As a result of the heating, however, different proton resonance frequencies are generated due to temperature differences of the heated tissue, and image aberration is created in MRI thermal images due to the spatial heat gradient around the ultrasound focal point. As a result, the ultrasound focal point as seen in the MRI thermal image (monitoring image) is different from the actual ultrasound focal point (the location of the corresponding target tissue). Accordingly, the ultrasound cannot accurately impinge onto the target tissue.

Figure 1:
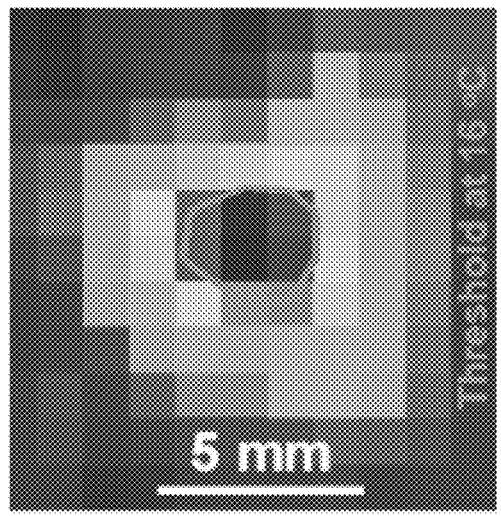
FIG. 1 illustrates a focal point of an MRI temperature map after chemical-shift correction.

The main causes for the spatial displacement between the ultrasound focal point as seen in the MRI thermal image and the actual ultrasound focal point are as follows:

The First Cause is "Chemical Shift":

Chemical shift originates from the different Larmor frequencies of the heated tissues such that the focal point appears spatially displaced. Referring to FIG. 1, the chemical shift correction results in the spatial shifting of 0.56 mm from the originally uncorrected center to the corrected center of focal point. However, such correction is insufficient to account for the total amount of error observed in clinical settings. Additional corrections are required.

Figure 2:
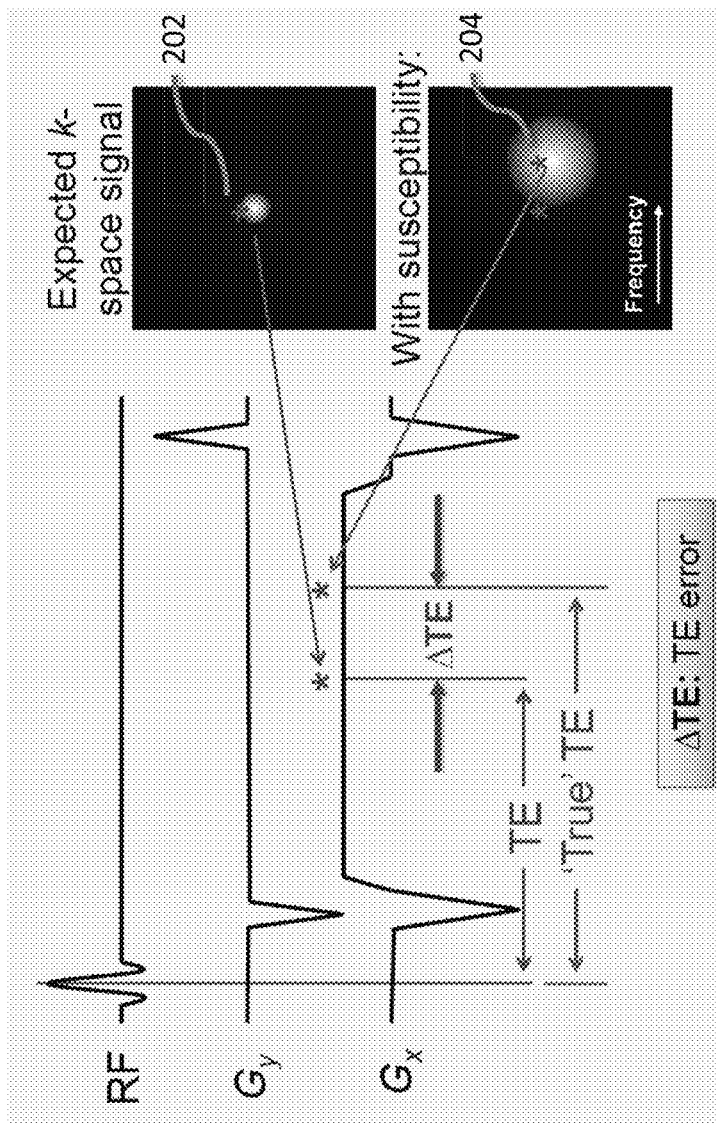
FIG. 2 illustrates a diagram showing that an error in k-space leads to an error in echo time.

The Second Case is "k-Space Shift":

K-space shift originates from spatial variations of Larmor frequency at two sides of the heated focal point, leading to spatial gradient in the phase image. After Fourier Transform, such spatial gradient of phase results in a shift of the MRI echo center in k-space (MRI's raw data). As shown in FIG. 2, the MRI echo (the main bulk of MRI signal) is expected to occur in the k-space center (star 202 located in the upper right image), but the k-space center is shifted (star 204 in the lower right image) as a result of the spatial change of Larmor frequency due to the heating-induced susceptibility effect. This shift of echo center in k-space directly leads to the error in TE, since the nominal TE user prescribed on the MRI GUI is different from the true TE.

This TE error results in temperature error in proton resonance frequency (PRF) shift thermometry, because TE is one of the proportionality constants when the temperature is calculated. The formula is as following:

$$\Delta T(\vec{r}) = \Delta\emptyset(\vec{r})/(\gamma \alpha B_0 \cdot TE(\vec{r})) \quad \text{Formula (1)}$$

where $\Delta T(\vec{r})$ is the temperature change between the measured time frame and baseline at position $\vec{r}$, $\Delta\emptyset(\vec{r}) = \emptyset_i(\vec{r}) - \emptyset_0(\vec{r})$, $\emptyset_i(\vec{r})$ is the phase image of the measured $i^{th}$ time frame, $\emptyset_0(\vec{r})$ is the phase image of baseline, and $\Delta\emptyset(\vec{r})$ is the phase difference between the measured time frame and baseline, $\gamma$ is gyromagnetic ratio, $\alpha$ is the heating-induced PRF change coefficient, $B_0$ is the main magnetic field strength, $TE(\vec{r})$ is the true, corrected echo time at position $\vec{r}$.

As shown in FIG. 3a, the spatial temperature gradient has opposite polarity at two sides of the focus, leading to opposite polarity of TE error at the two sides of the focus (FIG. 3b). The resultant temperature error also has opposite polarity at two sides of the focus (as shown in FIG. 3a). This means that the temperature is overestimated at one side of the focus and underestimated at the other side of the focus. Therefore, in addition to chemical-shift correction, the focus location must be further corrected by k-space shift correction.

Based on description above, the k-space shift comes from the heating-induced susceptibility gradient. As shown in FIG. 3a, the gradient has opposite sign at two sides of the focus, leading to opposite sign of TE error on two sides of the focus (FIG. 3b). Based on the formula described above, the positive TE error causes temperature underestimation at the left side 302 of focus, while the negative TE error causes temperature overestimation at the right side 304 of focus. The correction of such temperature error at both sides of focus shifts the focus center. This explains why k-space shift would lead to focus shift.

In view of the above, embodiments of the present disclosure provide a system and a method to correct heating-induced spatial error of focus by adding k-space correction either before or after the chemical-shift correction, such that the real, physical focus can be properly aligned with the monitored, as-seen focus on the temperature map.

Figure 4B:
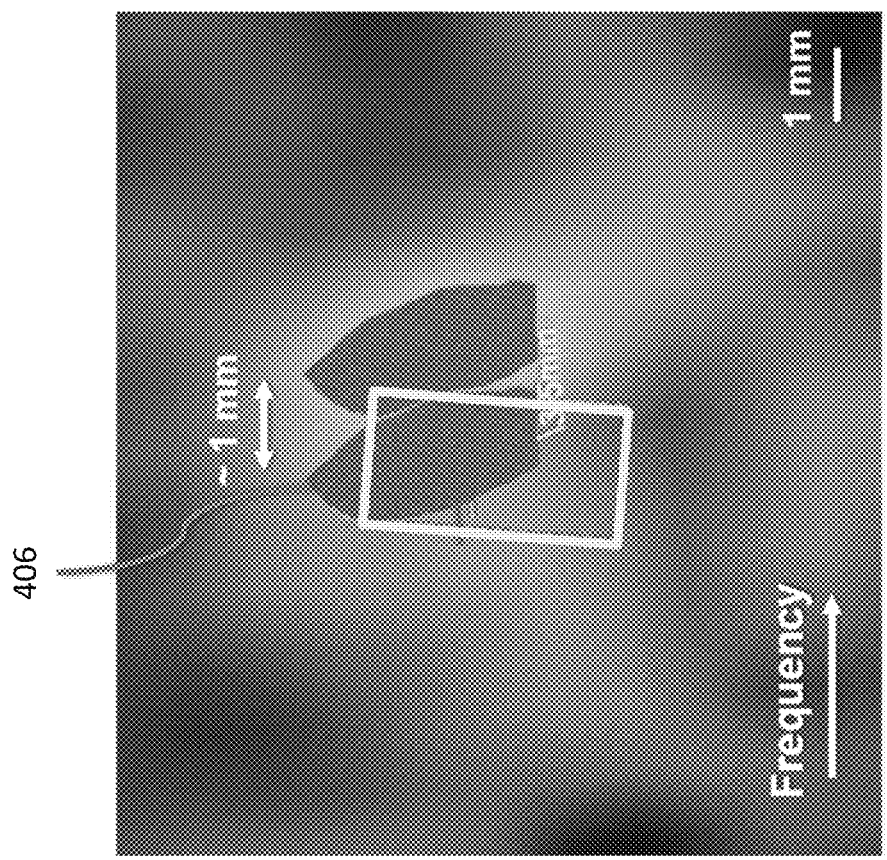
FIGS. 4a and 4b illustrate snapshots of a FUS GUI used in clinical trial, before and after a focus location is corrected.
Figure 4A:
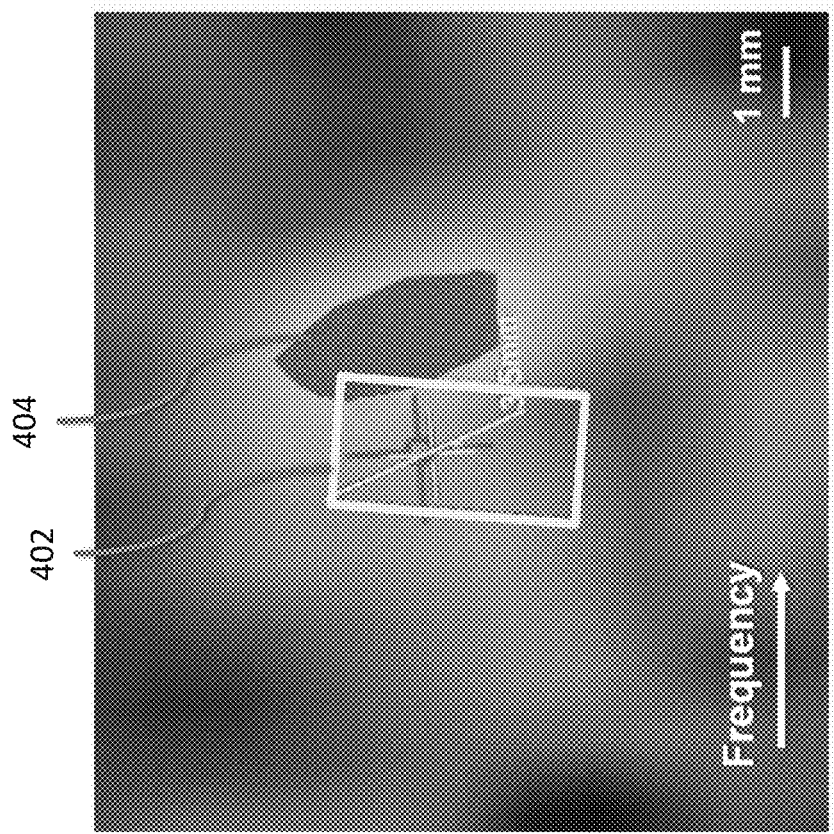

As shown in FIG. 4a, the rectangular box 402 indicates the actual location of the target tissue to be heated, while the solid mark 404 indicates the FUS focal point as seen on the thermal image. As shown in FIG. 4b, because the root causes of such spatial offset have been found, one can correct the spatial offset so as to properly align the monitored, as-seen focus on temperature map (solid mark 406) with the actual, physical focus of the FUS, thereby accurately impinging ultrasound to the target tissue.

To better understand the claimed invention in practice, the present disclosure is described in further detail using the clinical application in Essential Tremor (ET) treatment as an example. Such example, however, is not intended to limit the scope of the present disclosure. Rather, this claimed invention can be applied to any other MRgFUS applications, such as, uterus fibroid, bone metastasis, transcranial neurotomy, etc., where target tissue is to be thermally ablated.

In this example, following a patient's informed consent form, a physician treats the patient's Essential Tremor by using a focused ultrasound system under MR guidance. The ultrasound system includes a hemispheric, helmet-like, 650-kHz, 1024-element, phase array transducer (e.g., ExAblate Neuro commercially available from INSIGHTE of Israel) to transmit ultrasound energy in the patient's head and to a thalamus target in patient's brain. An MRI device 11 (e.g., 3T GE MRI) is used to monitor the heat dosage from the ultrasound energy transcranially delivered by the focused ultrasound system through the patient's skull. Exemplary MRI imaging parameters are listed below: FOV (field of view)=28×28 cm2, TE (echo time configured in MRI)=12.9 ms, TR (repetition time configured in MRI)=27.8 ms, matrix size (array dimension of MRI)=128×256, BW (MRI bandwidth)=±5.68 kHz.

In the treatment process, a plurality of low acoustic power sonications is delivered to progressively adjust the location of the focus. After the ultrasound focus is properly aligned, the neuro-surgeon gradually increases the FUS power until the tremor is treated and the surgery is completed. While increasing the heating power, the spatial error of FUS focus in the temperature map is corrected in real time, such that the focus location can be accurately displayed on MRI for the corresponding target tissue, thereby heating and ablating the target tissue.

Hereafter, the process of spatial error correction is described using the MRgFUS thalamotomy treatment performed on an ET patient as an example. Appendices I, II, and III provide a set of pseudo codes for performing the spatial error correction in accordance with an embodiment of the present disclosure.

Figures 5A, 5B, 5C, 5D, 5E, 5F:
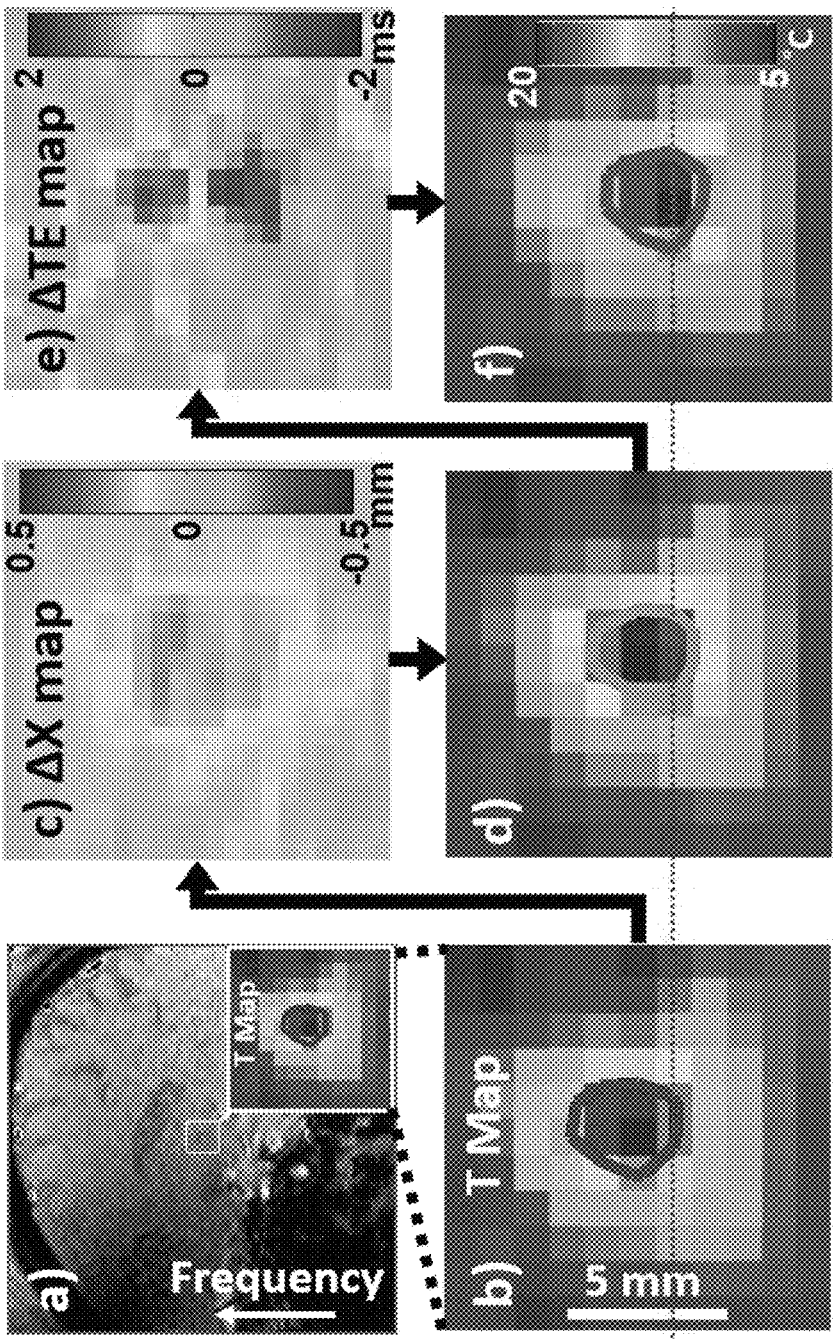
FIGS. 5a through 5f illustrate a flow diagram of chemical shift correction and k-space shift correction in accordance with an embodiment of the present disclosure.

Referring to FIGS. 5a through 5d, in this example, the chemical-shift correction is done to correct the spatial error caused by the change in magnetic field due to temperature increase. Here, $\Delta B_0(\vec{r})$ denotes the magnetic field change at position $\vec{r}$ of the MRI image due to heating. The consideration of this parameter is required for correcting the chemical shift. In FIG. 5b, temperature map (or T Map) is derived from $\Delta B_0(\vec{r})$, based on which $\Delta X$ map, the size of heating-induced spatial error, can be calculated as shown in FIG. 5c, so as to move the ultrasound focus location, as shown in FIG. 5d.

Subsequently, k-space correction is performed following the chemical-shift correction. The gradient of phase-difference map in frequency encoding direction is used to calculate the TE error map or the $\Delta TE$ map (as shown in FIG. 5e). The TE error at position $\vec{r}$ is computed by:

$$\Delta TE(\vec{r}) = N_f \times \nabla_x(\Delta \phi(\vec{r}))/BW/2\pi \quad \text{Formula (2)}$$

where $\vec{r}$ denotes a location vector in the MRI thermal image; $\Delta TE(\vec{r})$ denotes the echo time error; $N_f$ is the thermal image matrix size along a frequency encoding direction; $\nabla_x(\Delta \phi(\vec{r}))$ is the spatial gradient of the phase difference at position $\vec{r}$ along the frequency encoding direction; $\Delta \phi(\vec{r})$ is the phase difference upon subtraction of the MRI thermal image prior to heating; and BW is the total receiver bandwidth of the acquired MRI thermal image.

As shown in FIG. 5f, a corrected MRI thermal image $T(\vec{r})$ is derived from the following TE correction:

$$TE(\vec{r}) = TE + \Delta TE(\vec{r}) \quad \text{Formula (3)}$$

where $TE(\vec{r})$ is the corrected echo time; TE is the nominal echo time initially defined on the MRI GUI; and $\Delta TE(\vec{r})$ is the TE error. The corrected echo time is the initially defined echo time plus the echo time error.

Figures 6A, 6B, 6C, 6D:
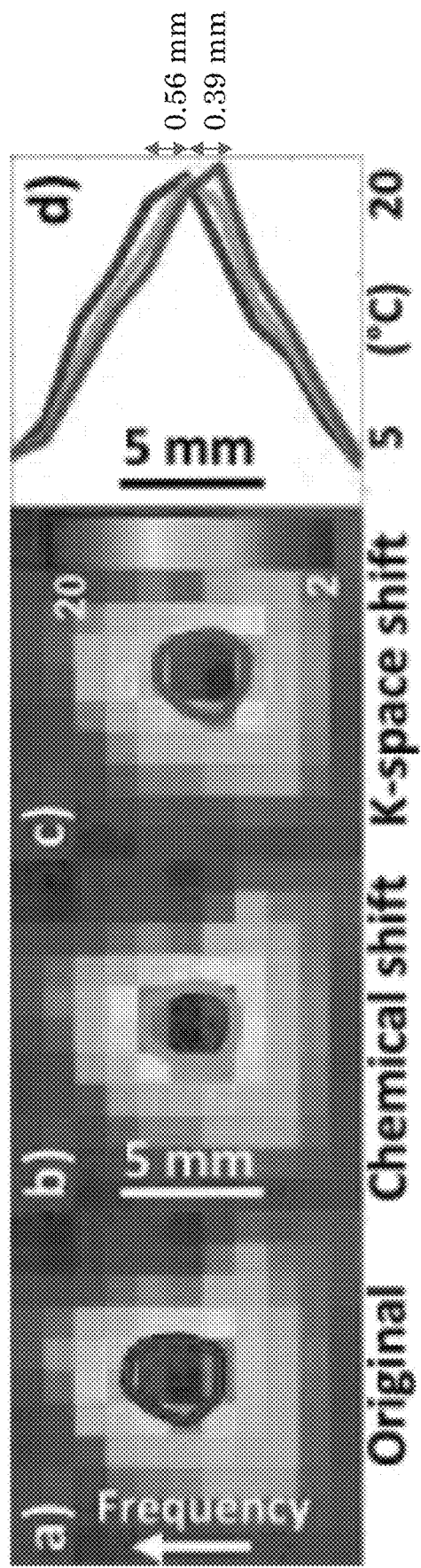
FIGS. 6a through 6d illustrate focus locations before correction, after chemical shift correct, and after both chemical-shift correction and k-space shift correction, in accordance with an embodiment of the present disclosure.

In summary, referring to FIGS. 6a through 6d, the center of ultrasound focus is shifted by a total of 0.95 mm (the distance between the contour centers in FIG. 6a and FIG. 6c). The center of focus in the original T map is first shifted by 0.56 mm after the chemical shift correction (from FIG. 6a to FIG. 6b), while the center of focus is additionally shifted by 0.39 mm after the k-space shift correction (from FIG. 6b to FIG. 6c), totaling 0.95 mm. This result is much closer to the clinically observed discrepancy (~1 mm) between the target object and the ultrasound energy focus.

Using the correction method described above, data associated with 121 sonications from seven Essential Tremor patients treated by the MRgFUS thalamotomy are statistically analyzed. The patient demographics and sonication statistics are listed in below Table 1.

TABLE 1

Patient demographics and sonication statistics.
Patient demographics and sonication statistics

|  | Study population |
|---|---|
| Total number of patients | 7 |
| Total number of sonications | 121 |
| Gender |  |
| Male | 7 |
| Femal | 0 |

TABLE 1-continued

Patient demographics and sonication statistics.
Patient demographics and sonication statistics

|  | Study population |
|---|---|
| Age (y) |  |
| Mean ± SD | 67.9 ± 6.3 |
| Median (min, max) | 68 (58, 78) |
| Sonication number per patient |  |
| Max T* < 5° C. | 3 ± 4 |
| 5 < Max T < 10° C. | 4 ± 2 |
| 10 < Max T < 15° C. | 4 ± 2 |
| Max T > 15° C. | 6 ± 3 |
| Total number | 17 ± 5 |
| Focus shift (mm) |  |
| Max T < 5° C. | 0.6 ± 0.4** |
| 5 < Max T < 10° C. | 0.3 ± 0.1 |
| 10 < Max T < 15° C. | 0.5 ± 0.2 |
| Max T > 15° C. | 0.9 ± 0.2 |

*Max T is the maximum temperature in focus during sonication.
**Focus shift may not be correct if Max T <5° C. (see context).

Figure 7:
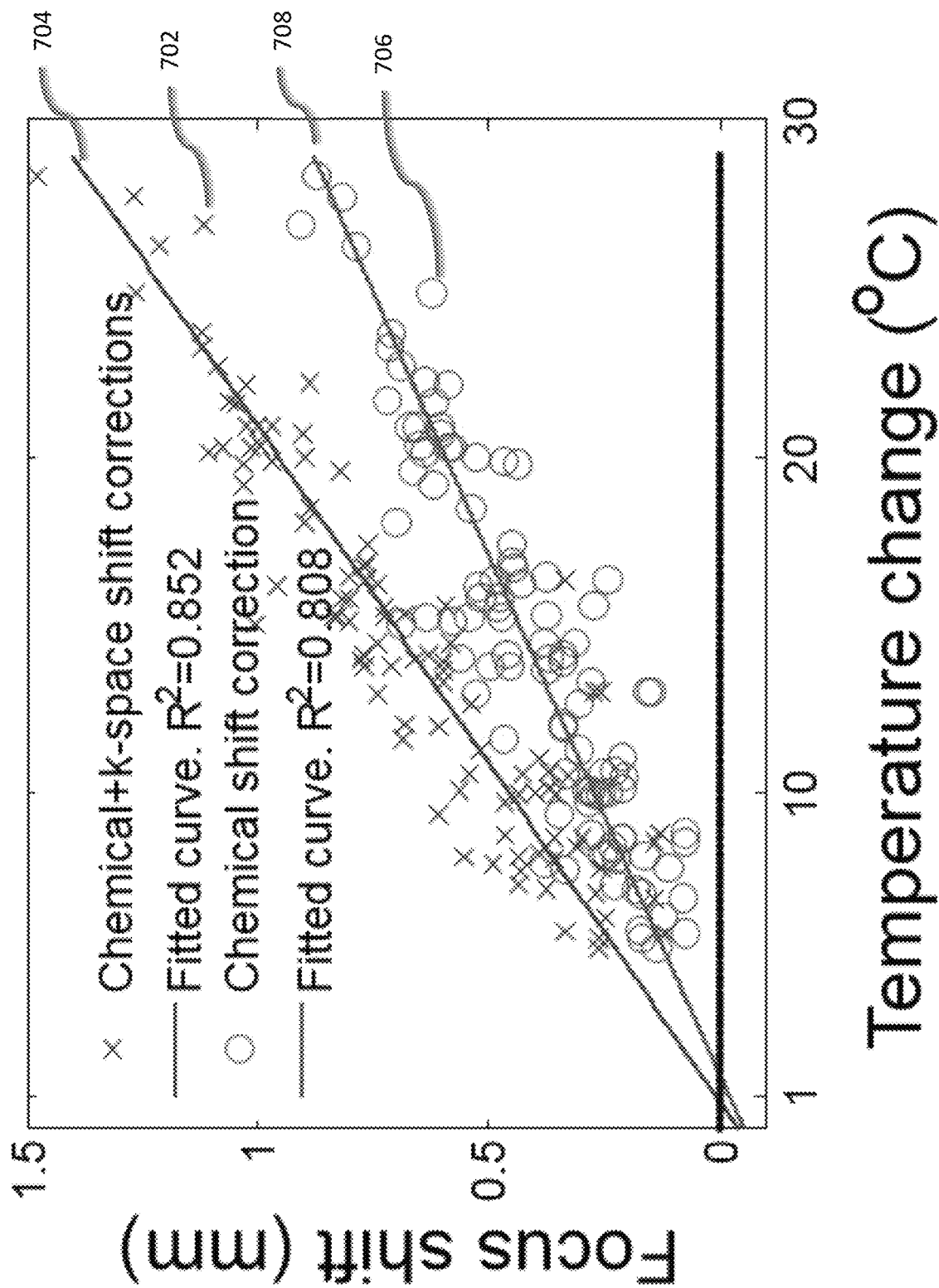
FIG. 7 illustrates a correlation analysis of spatial errors versus the heating temperature change at the focal point, after the chemical shift correction and the k-space correction in accordance with an embodiment of the present disclosure.

In accordance with Table 1, one can compare the correlation between heating temperature change and focus shift using the conventional chemical shift correction and using the correction method of the present disclosure (as shown in FIG. 7). In FIG. 7, 22 out of 121 sonications are excluded because: only minimum heat was produced (<5° C.), or cavitation was detected, or the surgeon stopped the sonication out of safety concerns, or the patient himself stopped the sonication, leaving 99 sonications for further analysis. A strong correlation ($R^2=0.852$) is found between temperature elevation and total focus shift using the correction method of the present disclosure (the blue crosses 702 and the blue line 704). The maximum spatial error is 1.5 mm occurred at 28.4° C. of sonication. From the fitted slope, an error of about 0.5 mm in focus location is expected for every 10° C. of temperature elevation. The conventional chemical shift correction method (the red circles 706 and the red line 708) can only account for about one half of the observed shift, while adding k-space shift correction to the chemical-shift correct can correct the focus shift at an average of 0.05 mm/° C. In other words, this claimed invention resolves the insufficient correction issue when only the traditional conventional chemical-shift correction is used.

Figures 8A, 8B:
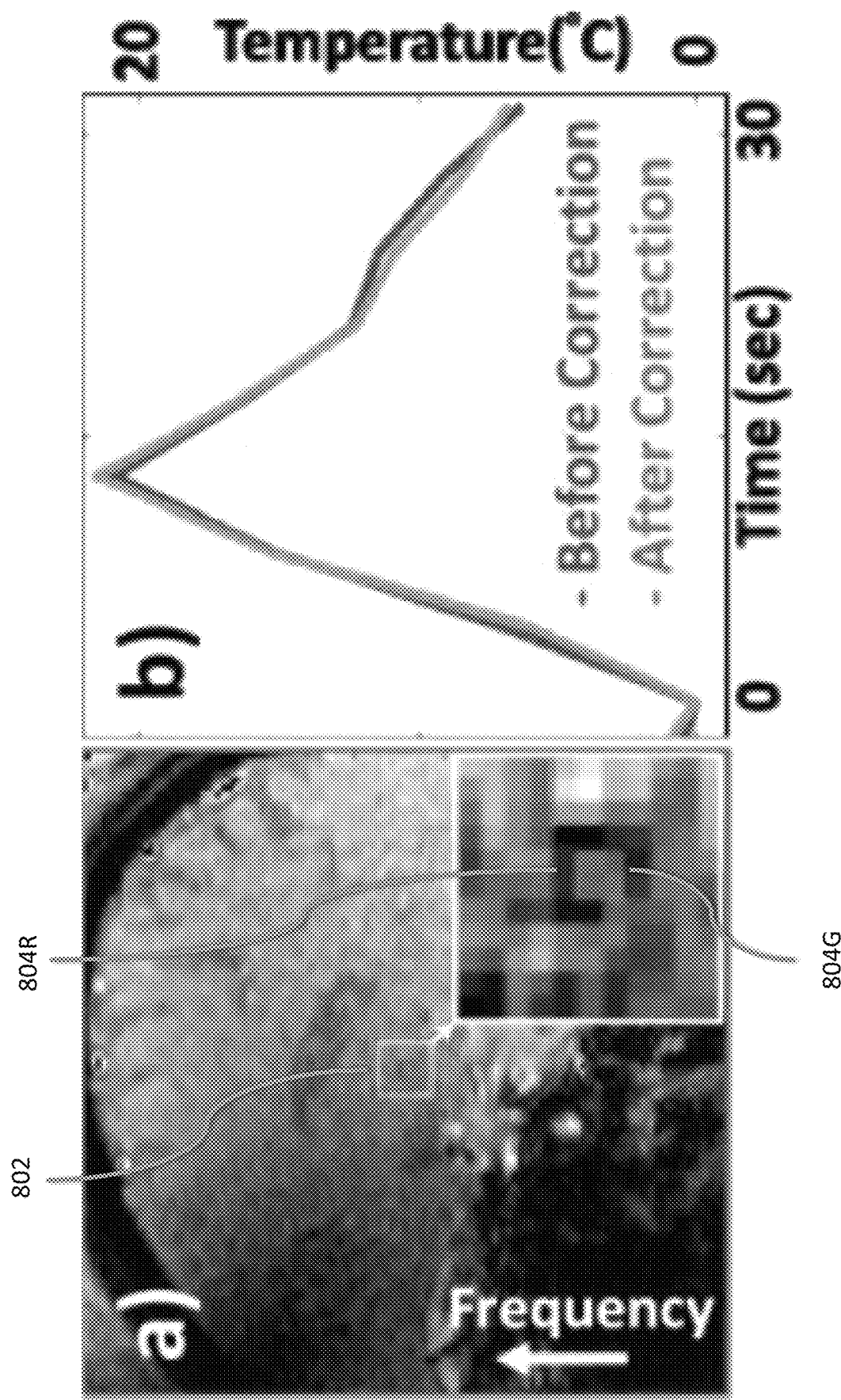
FIGS. 8a and 8b illustrate a temporal behavior of the focal point temperature in an MRI thermal image before and after the corrections.

To better understand whether the correction method of the present disclosure (both the chemical-shift and k-space shift corrections) would affect the temperature value at the focal center, please refer to FIGS. 8a and 8b. In FIG. 8a, the central box 802 indicates a location of the thalamotomy heated by ultrasound, an enlarged view of which is shown in the lower right corner of FIG. 8a, wherein the red portion 804R indicates the original focal point without correction, while the green portion 804G indicates the focal point after both the chemical shift correction and the k-space shift correct. FIG. 8b shows the relation between heating time and heating temperature at the focal center before and after the correction. From FIG. 8b, it is confirmed that the heating temperature and time behaviors are similar before and after the correction. Accordingly, the correction method of the present disclosure does not affect the temperature value at the focal point.

In addition, referring to FIGS. 9a and 9b, where both images 902 at the left column are thermal maps before correction. Further, the image 904 is a thermal map after sequential performance of (1) chemical shift correction and (2) k-space correction, while image 906 is a thermal map after sequential performance of (1) k-space correction and (2) chemical shift correction, looking from the perspective of ultrasound focal point in the MRI thermal image. As shown in FIGS. 9a and 9b, regardless of whether the chemical shift correction is performed before or after the k-space correction, the resultant differences are almost negligible. Therefore, the order of chemical shift correction and k-space correction does not affect the correction results.

Moreover, the present disclosure provides a system 100 for correcting spatial error of focus in temperature map for MRgFUS surgery (as shown in FIG. 10). In this embodiment, the system includes a computer device 13, an MRI device 11, and a FUS heating device 12. MRI device 11 scans patient and generates image data. When FUS heating device 12 is used to perform a heating treatment, computer device 13 collects MRI data, generates MRI thermal images, and controls FUS heating device 12 to align the ultrasound focal location to the actual location of the target tissue, in accordance with the chemical-shift correction and k-space correction results. Lastly, the computer device 13 displays the corrected location of the ultrasound focus on the MRI thermal image.

Further, the present disclosure provides a method for using the system 100 described above to correct the spatial error in MR thermometry for MRgFUS surgery. In one embodiment, the method includes: using MRI device 11 to generate a patient's MRI image data, using computer device 13 to receive the patient's MRI image data from MRI device 11 and display the correct focus location. While FUS heating device 12 introduces focused ultrasound energy to the expected focus location of FUS through a patient's body, computer device 13 aligns the ultrasound focal point in the MRI image to the actual ultrasound focal point of the target tissue in accordance with the result of chemical shift and k-space shift corrections. Further, FUS heating device 12 heats and ablates the target tissue based on the actual ultrasound focus location, while the focus location is monitored and corrected in real time for every single image in each heating process.

To summarize, the well-known "chemical-shift" effect is insufficient to account for the observed spatial error of focus in clinical settings for MRgFUS surgery. It only deals with the magnetic field change caused by the heating. The gradient of the heating-induced magnetic field change also needs to take into account, namely, the k-space shift effect. The k-space shift is used to correct temperature error at a single pixel of the temperature map. Prior to this claimed invention, it was believed that each pixel of a temperature map would have substantially the same amount of k-space shift during a global heating event. As such, no further spatial errors would be observed and corrected in addition to the chemical shift. However, focal heating in a HIFU surgery is a local heating event. To the inventor's best knowledge, no one has ever noticed that the pixel-to-pixel correction of k-space shift in temperature map of HIFU surgery would end up with a correction of spatial shift in focus. In other words, the k-space shift was conventionally used to correct temperature along temporal dimension, whereas this claimed invention corrects the temperature in spatial dimension. Therefore, the claimed invention corrects the spatial errors caused by both chemical-shift and k-space-shift effects. The correction amount is about 1 mm for temperature change of 20° C. in focus, which is in agreement with the observation in clinical settings. This claimed invention does not require any modification to current pulse sequence or imaging protocol, proving a straightforward method for accurate FUS targeting in MRgFUS surgery.

For the purposes of describing and defining the present disclosure, it is noted that terms of degree (e.g., "substantially," "slightly," "about," "comparable," etc.) may be utilized herein to represent the inherent degree of uncertainty that may be attributed to any quantitative comparison, value, measurement, or other representation. Such terms of degree may also be utilized herein to represent the degree by which a quantitative representation may vary from a stated reference (e.g., about 10% or less) without resulting in a change in the basic function of the subject matter at issue. Unless otherwise stated herein, any numerical values appeared in this specification are deemed modified by a term of degree thereby reflecting their intrinsic uncertainty.

Although various embodiments of the present disclosure have been described in detail herein, one of ordinary skill in the art would readily appreciate modifications and other embodiments without departing from the spirit and scope of the present disclosure as stated in the appended claims.

APPENDIX I

Main Code

```
%% read image parameters
fov = 280*1e-3;                          % field of view in m
TE = 12.884 * 1e-3;                      % echo time in s
TR = 27.804 * 1e-3;                      % repetition time in s
Nx = 256;                                % matrix size in phase encoding DIR
Ny = 256;                                % matrix size in freq. encoding DIR
Nz = 1;                                  % number of acquisition slice
BW = 5.68 * 1e3;                         % receiver bandwidth in Hz
Nt = 10;                                 % number of time frames
Ncoils = 1;                              % number of receiver coil
SZ_per_pix=fov*1000/Ny;                  % pixel size in mm
BW_per_pix = BW*2/Ny;                    % receiver bandwidth per pixel in Hz
%% load patient data
importdata([stem1, '037\phasedata.m']);
data_buf = ans;
importdata([stem1, '037\I.001.hdr']);
hdr = ans;
%% add dim for coil for data to be (Ny, Nx, Nz, Ncoil, Nt)
data = permute(data_buf, [1 2 4 5 3]);
%% load previously prepared mask
Load
    Z:\Research\data\ES_data\ES_patient_20160728\044\msk_Cor_brain_044
    .mat
%% calculate phase difference
```

APPENDIX I-continued

Main Code

```
dpmap = (data./repmat(data(:, :, 1, 1, 2), [1 1 1 1 Nt]));
phasedata = angle(dpmap).*repmat(msk, [1 1 1 1 10]);
%%% phase unwrap
[Ny, Nx, N_sl, Ncoils, Nt] = size(phasedata);
for iter = 1:2;                        % doing 2 iterations ensure the success of unwrap
    [buf buf] = phase_unwrap(phasedata, phasedata, Nx, Ny, Ncoils, Nt);
    phasedata = buf;
end
%%% calculate temperature map
Tmap = phasedata./(0.01*128*2*pi*TE);       % Formula (1)
%%% pick a region of 21 by 21 around focus for better visual display of focus shift
[fy fx ft] = search_max_heat(squeeze(Tmap), 10);
x = fx-5:fx+5;
y = fy-5:fy+5;
maxT = Tmap(fy, fx, 1, 1, ft); % maximum temperature in focus along all time
    frames
%%% temperature map unwarp (chemical shift correction)
for it = 1:Nt
  [Tmap_uw(:, :, 1, 1, it) dX_uw] = tmap_unwarp(BW_per_pix, Tmap0(:, :, 1, 1, it), 1,
    0, SZ_per_pix, 'y'); % details of this function are included in Subroutine A as
    shown in Appendix II
end
%%% temperature map correction (k-space shift correction)
[Tmap_uw_c dTE_uw_c] = tmap_correct(Tmap_uw, TE, BW_per_pix, Ny, 'y'); %
    details of this function are included in Subroutine B as shown in Appendix III
%%% draw contour around focus to show the difference before and after correction
[area0 centroid0] = DrawContour(Tmap0(:, :, 1, 1, ft), tmp_threshold, 'g', 4,
    SZ_per_pix, 1);
[area1 centroid1] = DrawContour(Tmap_uw(:, :, 1, 1, ft), tmp_threshold, 'g', 4,
    SZ_per_pix, 1);
[area2 centroid2] = DrawContour(Tmap_uw_c(:, :, 1, 1, ft), tmp_threshold, 'g', 4,
    SZ_per_pix, 1);
disp(['Focus shift in (x, y) direction is: (', num2str(centroid2-centroid0), ') mm']);
figure
cc = ceil(size(Tmap0, 2)/2);
plot(Tmap0(:, cc, 1, 1, ft), 'b'); hold on
plot(Tmap_uw(:, cc, 1, 1, ft), 'g')
plot(Tmap_uw_c(:, cc, 1, 1, ft), 'r')
legend('Original', 'After Freq.-shift correction', 'After TE error correction')
```

APPENDIX II

Subroutine A: tmap_unwarp

```
function [tmap_uw dX] = tmap_unwarp(BW_per_pix, tmap, s, shift, SZ_per_pix,
freq_DIR)
% To unwarp temperature map caused by chemical shift effect
% fmap is 2D field map, e.g.128x128, in Tesla
% BW_per_pix: Bandwidth per pixel (in Hz)
% tmap is 5D images to warp: e.g. 128x128x1x8x40 (Ny, Nx, Nz, Ncoils, Nt)
% shift is the number of pixels to shift. +: move to ascending DIR
% s is 1: shift to ascending DIR (right or down); -1: descending DIR
% SZ_per_pix: pixel size in mm
% freq_DIR: frequency direction
%%% freq DIR
if freq_DIR == 'y'
    tmap = permute(tmap, [2 1 3 4 5]);
end
%%% imaging parameters and some constants
gamma = 42.576;                              % gyromagnetic ratio in MHz/T
%alpha = 0.01*3*gamma;                       % Thermal coefficient
Ny = size(tmap, 1);                          % All images assumed to have same Ny
Nx = size(tmap, 2);                          % All images assumed to have same Nx
Ncoils = size(tmap, 4);
Nt = size(tmap, 5);
%%% Calculate the amount of warping required
[X Y] = meshgrid(1:Nx, 1:Ny);
dX = zeros(Ny, Nx);                          % Unwarped, version of X is X_uw (= X + dX)
X_uw = zeros(Ny, Nx);
num_iter = 4;                                % Number of iterations
tm = tmap;                                   % Pick right T map
for i = 1:Nx
    for j = 1:Ny
```

APPENDIX II-continued

Subroutine A: tmap_unwarp

```
% Iterate
        X_uw(j, i) = X(j, i);                           % Zeroth iteration, dX = 0
        for it = 1:num_iter
% Find field offset value at this particular location
            xm = floor(X_uw(j, i));                     % Nearest pixel, -x direction
            xp = ceil(X_uw(j, i));                      % Nearest pixel, +x direction
            xm = max(xm, 1);                            % Sanity check
            xp = min(xp, Nx);                           % Sanity check
            valm = tm(j, xm);
            valp = tm(j, xp);
            wm = 1 - (X_uw(j, i)-xm);
            wp = 1 - (xp-X_uw(j, i));
            f = (wm*tm(j, xm) + wp*tm(j, xp))/(wm+wp);  % Interpolate
% Find the dX associated with this field value
            dx = -s*f*alpha*SZ_per_pix/BW_per_pix;
            dX(j, i) = dx - shift;
            dX(j, i) = max(dX(j, i), -i+1);             % Sanity check
            dX(j, i) = min(dX(j, i), Ny-i);             % Sanity check
            X_uw(j, i) = X(j, i) + dX(j, i);
        end
    end
end
%%% Apply the warping
tmap_uw = zeros(size(tmap));
for t = 1:Nt
    for j = i:Ny
        tmap_uw(j, :, 1, 1, t) = spline(X(j, :), tmap(j, :, 1, 1, t), X_uw(j, :));
    end
end
%%% freq DIR
if freq_DIR == 'y'
    tmap_uw = permute(tmap_uw, [2 1 3 4 5]);
    dX = permute(dX, [2 1 3 4 5]);
end
```

APPENDIX III

Subroutine B: tmap_correct

```
function [tmap_c dTE] = tmap_correct(tmap, TE, BW_per_pix, Nx, freq_DIR)
% To correct temperature map pixel-to-pixel, caused by k-space shift
% tmap: temperature map to be corrected
% Nx: spatial resolution in frequency direction
% freq_DIR: frequency encoding direction
%%% freq DIR
if freq_DIR == 'y'
    tmap = permute(tmap, [2 1 3 4 5]);
end
%%% acquire needed info
Nt = size(tmap, 5);
%%% regain phase map
phasedata = tmap*(0.01*128*2*pi*TE);         % Derived from Formula (1)
%%% compute gradient of phase map
[gradx grady] = gradient(phasedata);
%%% calculate k-space shift map
dk = gradx*Nx/2/pi;
%%% calculate TE error map
dTE = dk/(BW_per_pix*Nx);                    % Formula (2)
%%% get corrected temperature map
newTE = TE + dTE;                            % Formula (3)
tmap_c = phasedata./(0.01*128*2*pi*newTE);
%%% freq DIR
if freq_DIR == 'y'
    tmap_c = permute(tmap_c, [2 1 3 4 5]);
    dTE = permute(dTE, [2 1 3 4 5]);
end
```

What is claimed is:

1. A method for determining an ultrasound focus location in a thermal image, the method comprising:
   obtaining a magnetic resonance thermal image of a tissue heated by a focused ultrasound; and
   correcting a chemical shift and a k-space shift of a monitored ultrasound focus location in the magnetic resonance thermal image such that the monitored ultrasound focus location is aligned with a real physical ultrasound focus location;
   wherein correcting the chemical shift comprises correcting a first spatial error of the monitored ultrasound focus location caused by resonance frequency changes of hydrogen nuclei due to environmental differences of water molecules;
   wherein correcting the k-space shift comprises correcting a second spatial error of the monitored ultrasound focus location caused by temperature error due to spatial variations of a primary magnetic field;
   wherein the magnetic resonance thermal image is a two-dimensional temperature map having M-by-N pixels, where M and N are natural numbers;
   wherein correcting the second spatial error comprises correcting a temperature error for each of the M-by-N pixels of the two-dimensional temperature map based on a corrected echo time;
   wherein the temperature error is derived from the following formula:

$$\Delta T(\vec{r}) = \Delta \emptyset(\vec{r})/(\gamma \alpha B_0 \cdot TE(\vec{r}))$$

where $\Delta T(\vec{r})$ is a temperature change between a measured time frame and a baseline at position $\vec{r}$, $\Delta \emptyset(\vec{r})$ is a phase difference between the measured time frame and the baseline, $\gamma$ is a gyromagnetic ratio, $\alpha$ is a heating-induced proton resonance frequency (PRF) change coefficient, $B_0$ is a main magnetic field strength, and $TE(\vec{r})$ is the corrected echo time of one of the M-by-N pixels at position $\vec{r}$; and wherein the corrected echo time at position $\vec{r}$ is derived from the following formula:

$$TE(\vec{r})=TE+\Delta TE(\vec{r})$$

where TE is a nominal echo time initially defined by a user, and $\Delta TE(\vec{r})$ is an echo time error at position $\vec{r}$ wherein the echo tune error at position is defined by the following formula:

$$\Delta TE(\vec{r})=N_f \times \nabla_x(\Delta\emptyset(\vec{r}))/BW/2\pi$$

where $N_f$ is a matrix size of the magnetic resonance thermal image along a frequency encoding direction, $\nabla_x(\Delta\emptyset(\vec{r}))$ is a spatial gradient of a phase difference at position $\vec{r}$ along the frequency encoding direction, $\Delta\emptyset(\vec{r})$ is a phase difference upon subtraction of the magnetic resonance thermal image prior to heating, and BW is a total receiver bandwidth of the magnetic resonance thermal image.

2. The method of claim 1, wherein correcting the chemical shift and the k-space shift comprises correcting the chemical shift either before or after correcting the k-space shift.

3. An apparatus for thermally ablating a tissue, the apparatus comprising:
   a focused ultrasound device configured to generate focused ultrasound so as to heat a target tissue at an actual ultrasound focus location of the focused ultrasound;
   a magnetic resonance imaging device configured to generate a magnetic resonance imaging data of the target tissue; and
   a computer device configured to generate a magnetic resonance thermal image based on the magnetic resonance imaging data so as to display a monitored ultrasound focus location of the focused ultrasound on the magnetic resonance thermal image;
   wherein the computer device is further configured to correct a chemical shift and a k-space shift of the monitored ultrasound focus location in the magnetic resonance thermal image such that the monitored focus location is aligned with the actual ultrasound focus location;
   wherein the chemical shift is corrected by calculating a first spatial error of the monitored ultrasound focus location caused by resonance frequency changes of hydrogen nuclei due to environmental differences of water molecules;
   wherein the k-space shift is corrected by calculating a second spatial error of the monitored ultrasound focus location caused by temperature error due to spatial variations of a primary magnetic field;
   wherein the magnetic resonance thermal image is a two-dimensional temperature map having M-by-N pixels, where M and N are natural numbers;
   wherein the computer device is further configured to calculate a temperature error for each of the M-by-N pixels of the two-dimensional temperature map based on a corrected echo time so as to determine the second spatial error;
   wherein the temperature error is derived from the following formula:

$$\Delta T(\vec{r})=\Delta\emptyset(\vec{r})/(\gamma\alpha B_0 \cdot TE(\vec{r}))$$

where $\Delta T(\vec{r})$ is a temperature change between a measured time frame and a baseline at position $\vec{r}$, $\Delta\emptyset(\vec{r})$ is a phase difference between the measured time frame and the baseline, $\gamma$ is a gyromagnetic ratio, $\alpha$ is a heating-induced proton resonance frequency (PRF) change coefficient, $B_0$ is a main magnetic field strength, and $TE(\vec{r})$ is the corrected echo time of one of the M-by-N pixels at position $\vec{r}$;
   wherein the corrected echo time at position $\vec{r}$ is derived from the following formula:

$$TE(\vec{r})=TE+\Delta TE(\vec{r})$$

where TE is a nominal echo time initially defined by a user, and $\Delta TE(\vec{r})$ is an echo time error at position $\vec{r}$; and
   wherein the echo time error at position $\vec{r}$ is defined by the following formula:

$$\Delta TE(\vec{r})=N_f \times \nabla_x(\Delta\emptyset(\vec{r}))/BW/2\pi$$

where $N_f$ is a matrix size of the magnetic resonance thermal image along a frequency encoding direction, $\nabla_x(\Delta\emptyset(\vec{r}))$ is a spatial gradient of a phase difference at position $\vec{r}$ along the frequency encoding direction, $\Delta\emptyset(\vec{r})$ is a phase difference upon subtraction of the magnetic resonance thermal image prior to heating, and BW is a total receiver bandwidth of the magnetic resonance thermal image.

4. The apparatus of claim 3, wherein the chemical shift is corrected either before or after the k-space shift is corrected.

5. A computer program product for determining an ultrasound focus location in a thermal image, the computer program product comprising a non-transitory computer readable medium having stored therein instructions when executed by a computer device causing the computer device to perform a method comprising:
   obtaining a magnetic resonance thermal image of a tissue heated by a focused ultrasound; and
   correcting a chemical shift and a k-space shift of a monitored ultrasound focus location in the magnetic resonance thermal image such that the monitored ultrasound focus location is aligned with a real physical ultrasound focus location;
   wherein correcting the chemical shift comprises correcting a first spatial error of the monitored ultrasound focus location caused by resonance frequency changes of hydrogen nuclei due to environmental differences of water molecules;
   wherein correcting the k-space shift comprises correcting a second spatial error of the monitored ultrasound focus location caused by temperature error due to spatial variations of a primary magnetic field;
   wherein the magnetic resonance thermal image is a two-dimensional temperature map having M-by-N pixels, where M and N are natural numbers;
   wherein correcting the k-space shift comprises calculating a temperature error for each of the M-by-N pixels of the two-dimensional temperature map based on a corrected echo time so as to determine the second spatial error;
   wherein the temperature error is derived from the following formula:

$$\Delta T(\vec{r})=\Delta\emptyset(\vec{r})/(\gamma\alpha B_0 \cdot TE(\vec{r}))$$

where $\Delta T(\vec{r})$ is a temperature change between a measured time frame and a baseline at position $\vec{r}$, $\Delta\emptyset(\vec{r})$ is a phase difference between the measured time frame and the baseline, $\gamma$ is a gyromagnetic ratio, $\alpha$ is a heating-induced proton resonance frequency (PRF) change coefficient, $B_0$ is a main magnetic field strength, and $TE(\vec{r})$ is the corrected echo time of one of the M-by-N pixels at position $\vec{r}$;

wherein the corrected echo time at position $\vec{r}$ is derived from the following formula:

$$TE(\vec{r}) = TE + \Delta TE(\vec{r})$$

where TE is a nominal echo time initially defined by a user, and $\Delta TE(\vec{r})$ is an echo time error at position $\vec{r}$; and wherein the echo time error at position $\vec{r}$ is defined by the following formula:

$$\Delta TE(\vec{r}) = N_f \times \nabla_x(\Delta\phi(\vec{r}))/BW/2\pi$$

where $N_f$ is a matrix size of the magnetic resonance thermal image along a frequency encoding direction, $\nabla_x(\Delta\phi(\vec{r}))$ is a spatial gradient of a phase difference at position $\vec{r}$ along the frequency encoding direction, $\Delta\phi(\vec{r})$ is a phase difference upon subtraction of the magnetic resonance thermal image prior to heating, and BW is a total receiver bandwidth of the magnetic resonance thermal image.

6. The computer program product of claim 5, wherein correcting the chemical shift and the k-space shift comprises correcting the chemical shift either before or after correcting the k-space shift.

\* \* \* \* \*